United States Patent [19]

Carriker et al.

[11] Patent Number: 4,944,722
[45] Date of Patent: Jul. 31, 1990

[54] PERCUTANEOUS AXIAL FLOW BLOOD PUMP

[75] Inventors: John W. Carriker; Richard K. Wampler, both of Gold River, Calif.

[73] Assignee: Nimbus Medical, Inc., Rancho Cordova, Calif.

[21] Appl. No.: 314,813

[22] Filed: Feb. 23, 1989

[51] Int. Cl.$^5$ .............................................. A61M 1/00
[52] U.S. Cl. .................................. 600/16; 128/DIG. 3; 604/151; 604/264; 415/900
[58] Field of Search .................... 600/16; 604/52, 151, 604/264; 128/DIG. 3; 623/3; 415/900

[56] References Cited

U.S. PATENT DOCUMENTS

| 4,135,253 | 1/1979 | Reich et al. | 415/900 |
|---|---|---|---|
| 4,589,822 | 5/1986 | Clausen et al. | 415/900 |
| 4,625,712 | 12/1986 | Wampler | 604/52 |
| 4,688,998 | 8/1987 | Olsen et al. | 600/16 |
| 4,704,121 | 11/1987 | Moise | 623/3 |
| 4,753,221 | 6/1988 | Kensey et al. | 604/52 |
| 4,779,614 | 10/1988 | Moise | 604/151 |
| 4,817,586 | 4/1989 | Wampler | 600/16 |
| 4,846,152 | 7/1989 | Wampler et al. | 128/DIG. 3 |

Primary Examiner—Stephen C. Pellegrino
Assistant Examiner—Michael Rafa
Attorney, Agent, or Firm—Weissenberger & Peterson

[57] ABSTRACT

The reliability and compactness of a percutaneously insertable intravascular axial flow blood pump are improved by connecting the pump's rotor and drive cable through a resiliently extendable rotor extension. The rotor extension and drive cable fitting are so designed that the thrust bearing surfaces of the purge seal and cable fitting can be preloaded by strongly pulling the cable fitting against the resiliency of the rotor extension to move one of the bearings away from the other, then relaxing it to a predetermined preload, and finally immobilizing the bearing in the position corresponding to that preload.

6 Claims, 2 Drawing Sheets

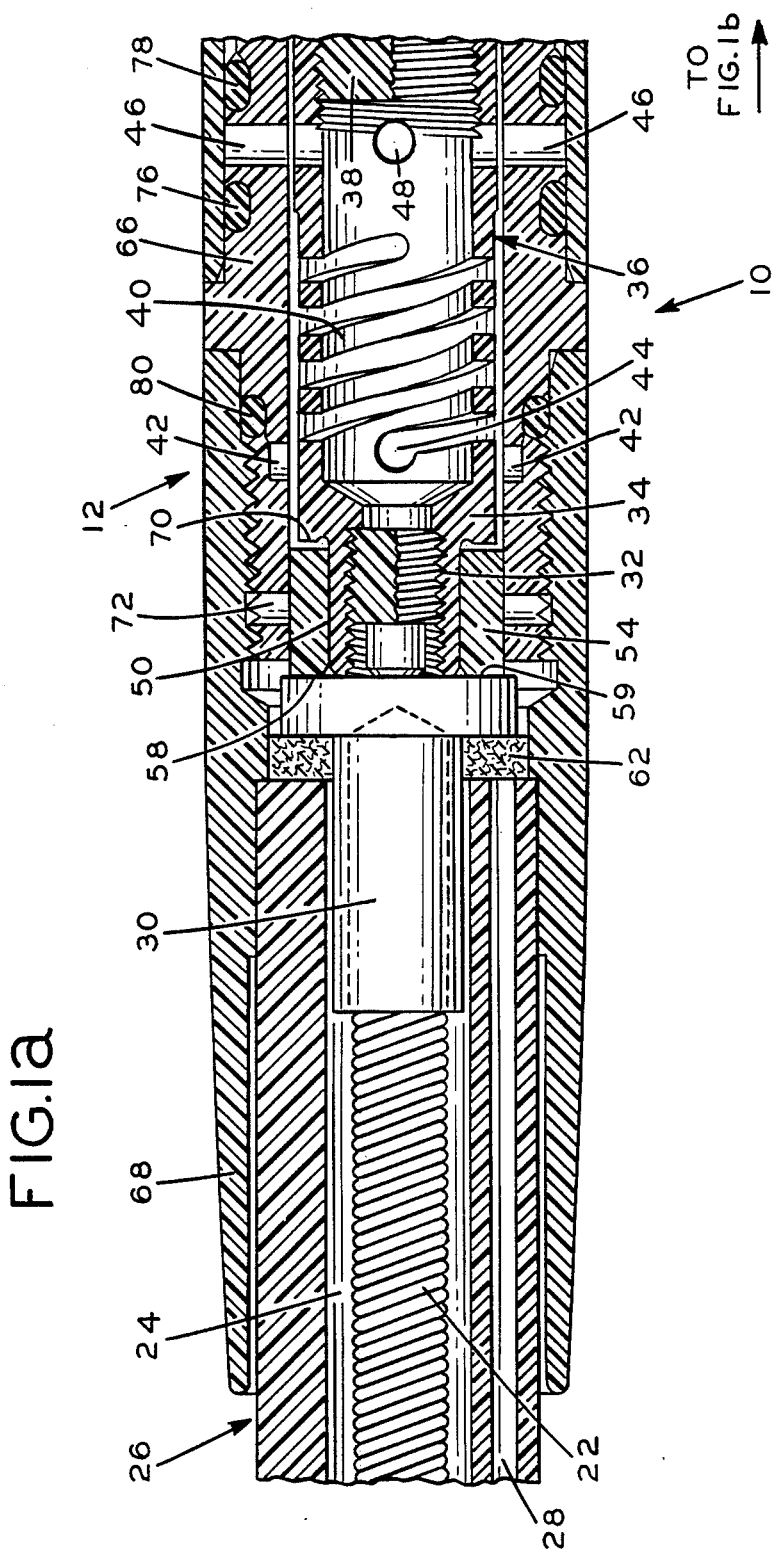

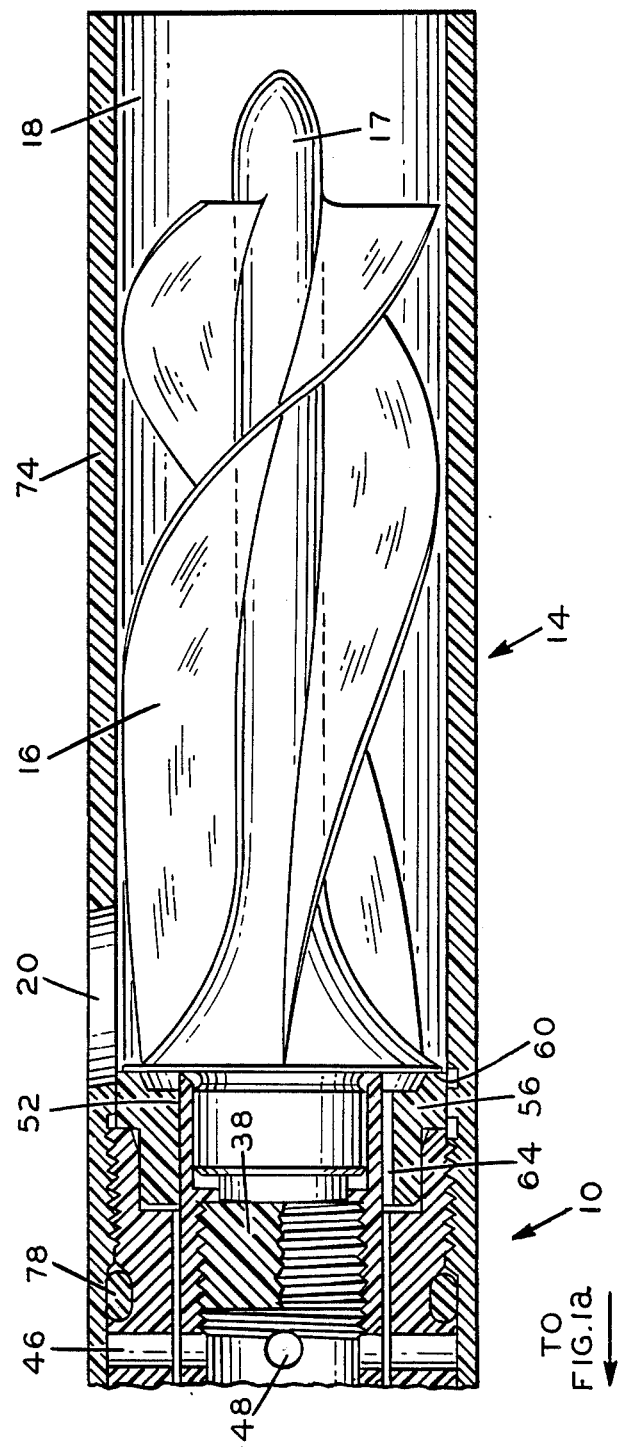

PERCUTANEOUS AXIAL FLOW BLOOD PUMP

FIELD OF THE INVENTION

This invention relates to miniature intravascular blood pumps, and more particularly to an improved axial flow pump which is smaller yet more rugged and reliable.

BACKGROUND OF THE INVENTION

U.S. Pat. No. 4,625,712 and U.S. patent application Ser. No. 07/124,560 disclose expendable miniature axial flow blood pumps adapted to be percutaneously inserted into the human vascular system for emergency cardiac assit purposes. Although these pumps have been quite successful in practice, there is a continuing need for reduction in size (e.g. in order to allow insertion through a standard large-diameter needle rather than through a surgical incision) as well as for improved ruggedness, reliability and ease of handling (e.g. in order to allow use by less skilled personnel), all at lesser cost.

SUMMARY OF THE INVENTION

The present invention provides an improved percutaneous blood pump with a preloaded spring arrangement which substantially simplifies the pump's design and fabrication and makes it easier and less delicate to handle.

Specifically, the arrangement of this invention has the following advantages: (1) it permits a shorter body construction which makes it easier to pass the pump through bends in the insertion cathether; (2) it makes the purge seal design predictable, thereby allowing lower thrust bearing loads and torque, and a consequent reduction in the size of the journal and thrust bearings; (3) runouts and stackup tolerances are less critical, and assembly can be automated, thereby reducing costs, and (4) the mass of plastic bearings is minimized to reduce deleterious effects such as thermal expansion and water absorption, and to allow a wider selection of more durable and less costly materials.

The heart of the present invention is a helical spring formed integrally with the rotor and connected to the drive cable, together with a movable bearing ring. This allows the thrust bearing to be preloaded during assembly to a precise predeterminable level.

BRIEF DESCRIPTION OF THE DRAWINGS

FIGS. 1a and 1b, taken together, constitute an axial section of a blood pump constructed in accordance with the invention.

DESCRIPTION OF THE PREFERRED EMBODIMENT

The percutaneously insertable intravascular axial flow blood pump 10 shown in the drawings, which is a pump of the general type disclosed in U.S. patent application Ser. No. 07/124,560, includes a stationary housing 12 and a rotor 14 equipped with a set of rotor blades 16. The hub 17 of rotor 14 is tapered at its downstream (left in the drawing) end so as to cause blood drawn into the upstream end 18 of pump 10 to be expelled in a mixed (partially axial, partially centrifugal) flow through circumferentially spaced discharge slots 20 (only one being shown in the drawings) in the wall of housing 12.

The rotor is driven by a cable 22 located in the drive cable lumen 24 of a two-lumen cable sheath 26. The second lumen 28 is a purge fluid supply conduit through which a blood-compatible lubricating fluid for the bearings of the pump 10 is supplied from an extracorporeal source. The cable 22 terminates in a fitting 30 whose head 32 can be screwthreadedly engaged with the nose 34 of an extension 36 of the hub 17 of rotor 14. The extension 36 is itself screwthreadedly engaged with the head 38 of the hub 17.

The extension 36 is a generally tubular member whose central section is cut to form a tension spring 40 which allows the extension 36 to be axially extended to permit the preloading characteristic of this invention. The extension 36 can be temporarily immobilized to permit thread engagement during assembly by the insertion of retaining pins (not shown) through openings 42, 44 and 46, 48, respectively. Surfaces 50, 52 of bearing rings 54, 56, respectively, form hydrodyanmic journal bearings for rotor 14. The interface surface 58 of ring 54 and the thrust runner 59 form a movable thrust bearing, and the interface seal bearing face 60 of ring 56 and the hub 17 form a fixed purge seal thrust bearing through which the bearing fluid is discharged into the blood stream.

As described in U.S. patent application Ser. No. 07/129,714, a portion of the purge fluid supplied through lumen 28 is returned through drive cable lumen 24 to flush that lumen and prevent abraded cable sheath fragments from entering the pump 10—a problem which is further prevented by the insertion of a filter ring 62 in the purge fluid path. The bearing rings 54, 56 are grooved as indicated at 64 to provide a path for the purge fluid to the seal 60.

The assembly of the pump 10 takes place as follows: First the extension 36 is inserted into the central portion 66 of housing 12 and is pinned through openings 42, 44, 46 and 48. Next, the rotor 14 and the cable fitting 30 are screwed tightly into the extension 36. The holding pins are then removed, and the cable fitting 30 (the cable sheath 26 and sheath retainer 68 not yet being in place) is pulled to the left with sufficient force to expand spring 40 and cause the shoulder 70 of extension 36 to push bearing ring 54 to the left beyond its operating position.

The tension on fitting 30 is now released to the point where it equals the desired bearing preload. The resulting pressure of fitting 30 against the thrust bearing surface 58 of ring 54 pushes ring 54 back to the right into its operating position, where it can be permanently immobilized by applying a bonding material through opening 72. When the tension on fitting 30 is then released, the preload on thrust bearings 58 and 60 will be precisely the desired amount.

The cable sheath 26 and the rotor shroud 74 can now be slipped over the cable 24 and rotor 14, respectively, and the sheath retainer 68 and rotor shroud 74 can be screwed onto the central housing portion 66 to complete the assembly of the pump 10.

It will be seen that the construction of this invention provides a constant, reliable purge pressure which is not affected by manipulation of the cable or sheath. The invention eliminates the need for seal head readjustment, and the lateral flexibility of the extension 36 allows independent alignment of the forward and aft bearings and the seal. All of these features greatly improve the ruggedness and reliablity of the pump 10. It will also be understood that in practice, the O-rings 76, 78, 80, as well as the screwthreads, can be replaced by bonding in automated assembly processes.

I claim:

1. A cable-driven percutaneous insertable intravenous axial flow blood pump preloadable to provide a substantially constant purge pressure unaffected by manipulation of the pump drive cable or cable sheath, comprising:

(a) a static housing;
   (b) a rotor disposed in said static housing;
   (c) a drive cable for driving said rotor, said drive cable terminating in a cable fitting having a thrust bearing surface;
   (d) rotor extension means for connecting said rotor to said drive cable through said static housing, said rotor extension means being resiliently extendable;
   (e) movable bearing means disposed in said static housing, said rotor extension being journalled in said bearing means, and said bearing means having thrust bearing surface means for mating with said cable fitting thrust bearing surface to form a thrust bearing;
   (f) shoulder means on said rotor extension means for engaging said movable bearing means when said extension is extended; and
   (g) means for selectively fixedly interconnecting said movable bearing means and said static housing to immobilize said movable bearing means within said static housing;
   (h) whereby said thrust bearing can be preloaded to a predetermined load by pulling said cable fitting to extend said extension with a force greater than said predetermined load, relaxing said force to said predetermined load, and then immobilizing said bearing means.

2. The pump of claim 1, in which said movable bearing means is a bearing ring axially slidable within said static housing.

3. The pump of claim 1, in which said rotor extension means is a substantially cylindrical member cut out so that a portion thereof forms a spring integral with said cylindrical member.

4. The pump of claim 1, in which said rotor extension means is screwthreadedly engageable with at least one of said rotor and cable fitting, and releasable holding means engaging said static housing and said rotor extension means are provided to temporarily immobilize said rotor extension means within said static housing during assembly with said rotor and cable fitting.

5. The pump of claim 1, wherein said static housing means has an opening adjacent to said bearing means, and bearing means immobilizing means is a bonding material introduced through said opening.

6. The pump of claim 1, further comprising fixed bearing means disposed in said static housing, said rotor extension means being sufficiently laterally flexible to allow independent alignment of said movable and fixed bearing means.

* * * * *